US005648266A

United States Patent [19]
Astle

[11] Patent Number: 5,648,266
[45] Date of Patent: Jul. 15, 1997

[54] CELL HARVESTER SYSTEM

[76] Inventor: Thomas W. Astle, 607 Harborview Rd., Orange, Conn. 06477

[21] Appl. No.: 314,791

[22] Filed: Feb. 24, 1989

[51] Int. Cl.⁶ .............................. C12M 1/12; C12M 1/00
[52] U.S. Cl. ..................... 435/308.1; 435/297.1; 435/305.1; 422/100; 422/101
[58] Field of Search ..................... 435/288, 287, 435/291, 310, 311, 30, 39, 308.1, 297.1, 305.1; 436/49, 52, 54; 422/100, 101, 102

[56] References Cited

U.S. PATENT DOCUMENTS

| | | | |
|---|---|---|---|
| 3,568,735 | 3/1971 | Lancaster | 422/100 |
| 4,201,845 | 5/1980 | Feder et al. | 435/285 |
| 4,245,042 | 1/1981 | Weinstein et al. | 435/30 |
| 4,383,041 | 5/1983 | Kutsusawa et al. | 435/288 |
| 4,493,896 | 1/1985 | La Motte, III et al. | 435/287 |

FOREIGN PATENT DOCUMENTS 7606 12/1986 WIPO.

OTHER PUBLICATIONS

Brochure on Skatron cell harvester and filterdisc transfer system by Skatron Inc., Sterling, Virginia (No Date).
Brochure on Brandel cell harvesters by Brandel, Gaithersburg, Maryland (No Date).
Brochure on PHD cell harvester by Cambridge Technology, Inc., Cambridge, Massachusetts (No Date).
Brochure on Skatron automatic microplate washers by Skatron Inc., Sterling VA (No Date).
Brochure on automated microplate washer by Bio–Tek Instruments, Inc., Burlington VT (No Date).
Brochure on microplate washer by SLT Labinstruments, Salzburg, Austria (No Date).
Brochure on automated wash system by Perkin–Elmer, Norwalk CT.

*Primary Examiner*—Jill Warden
*Assistant Examiner*—Jan M. Ludlow
*Attorney, Agent, or Firm*—John H. Crozier

[57] ABSTRACT

In a preferred embodiment, there is provided a cell harvester system, and method for operating the same, which furnishes a flow of wash solution into each of, for example, the 96 wells of a microplate. The contents of each well are aspirated to a specific area on a filter mat and the effluent is directed to one of two traps. Separate areas of the filter mat unique to each well are isolated by means of opposing O-rings. Due to the proximity of the sample wells (9 mm on center) there is the possibility of an overflow from one well contaminating adjacent wells. To prevent that occurrence, an aspirated overflow ring space is provided around each well. A microprocessor controlled system is used to sequence the various functions. To provide flexibility of control, the 96-well plate is treated as 8 separate 12-well systems (rows). Each row of 12 wells has its own overflow valve, wash valve, and aspirate valve. The control system can sequence any number or rows at a time and the control system can be set to select from one of a plurality of wash solutions.

5 Claims, 12 Drawing Sheets

CELL HARVESTER SYSTEM

BACKGROUND OF THE INVENTION

1. Field of the Invention.

The present invention generally relates to the class of laboratory instruments identified as cell harvesters and, more particularly, to a novel cell harvester system, and method of operating the same, which includes, inter alia, improved cell wall washing, aspiration of liquid overflow from individual cells, and control of wash, aspirate, and overflow in individual sets of cells. An operator-programmable microprocessor may be employed to control a number of parameters in selected sequences.

2. Background Art.

In the field of medical and biotechnology research, there is a need to mark various test components of interest. These components may be cells containing antigens, antibodies or other factors. The most common marking methods use enzymes and radioactive labels. Once the cells are marked, they must be separated from the unmarked components, and then read or assayed. The ease of counting radioactivity facilitates this method of labelling. The newer methods of liquid scintillation counting increase the sensitivity of the method, while reducing the amount of radioactivity required. To further reduce the volume of reagents used, and thus the waste generated, the newer test methods are typically based on 96-well microplates using microliter test quantities.

The common method of harvesting from the microplates is to aspirate the test components from each of the wells on the plate through a filter substrate. The particulate matter, labeled with a radioactive material, is trapped by the filter, and unwanted components are washed away. The filter substrate is then radioactively counted to assay the test results.

A line of instruments, commonly referred to as cell harvesters, is used for the purpose of transferring components to the filter mat.

The present cell harvester designs originated from test tube-based protocols. Today, the trend is to the use of microplates using 96 wells holding up to 300 microliters each in an 8×12 array on 9 mm centers. For greatest efficiency, it is desirable to harvest all 96 wells simultaneously or by various segments, and do it automatically. This need presents new and different design challenges for the cell harvester. It now becomes necessary to seal 96 flow passages to the filter substrate. The lower volume of the microwells (300 microliters) means more wash cycles are required, if the past methods are to be used.

Conventionally, the well or tube is filled with wash solution to bring all of the components in contact with the wash solution. Then, the liquid contents are aspirated to the filter mat. The well or tube is refilled, and the process repeated several times. With only a 300-microliter volume limit, a number of consecutive wash and aspirate cycles are required to pass sufficient wash solution through the filter mat.

Present designs bring the wash buffer to the well in one line and aspirate to the filter mat with a second line. If the wash and aspirate lines open concurrently, the wash solutions enters the well only to be attracted to the aspirate line without washing the sidewalls of the wells. Thus, the operator must either manually raise and lower the aspirate tube in relation to the bottom of the well, or use the consecutive wash-aspirate cycles described above.

As test protocols become more sophisticated, it is not enough just to wash the particulate matter to the filter mat. There is a need to control the amount and type of wash solution, the rate of flow, and drying the filter mat at the end or in-between washes. In summary, there is a need to automatically and precisely control all of the parameters in cell harvesting needs.

Accordingly, it is a principal object of the present invention to provide a cell harvester system which controls separately or in concert the functions of wash, aspirate, and overflow in all wells or selected wells of a laboratory tray.

Another object of the invention is to provide means to fully wash the walls of such wells while simultaneously aspirating the wash solution from the wells.

An additional object of the invention is to provide means to aspirate any liquid which overflows a well without the liquid overflowing into adjacent wells.

A further object of the invention is to provide means for isolating a unique area of filter medium for a selected well.

Yet another object of the invention is to provide a microprocessor-based control for a cell harvester system.

Other objects of the invention, as well as particular features and advantages thereof, will be apparent from the following description and the accompanying drawing figures.

SUMMARY OF THE INVENTION

The present invention accomplishes the above objects, among others, by providing in a preferred embodiment a cell harvester system, and method of operating the same, which furnishes a flow of wash solution into each of, for example, the 96 wells of a microplate. The contents of each well are aspirated to a specific area on a filter mat and the effluent is directed to one of two traps. Separate areas of the filter mat unique to each well are isolated by means of opposing O-rings. Due to the proximity of the sample wells (9 mm on center) there is the possibility of an overflow from one well contaminating adjacent wells. To prevent that occurrence, an aspirated overflow ring space is provided around each well.

A microprocessor controlled system is used to sequence the various functions. To provide flexibility of control, the 96-well plate is treated as 8 separate 12-well systems (rows). Each row of 12 wells has its own overflow valve, wash valve, and aspirate valve. The control system can sequence any number of rows at a time and the control system can be set to select from one of a plurality of wash solutions.

DETAILED DESCRIPTION OF THE PREFERRED EMBODIMENTS

Figure 1:
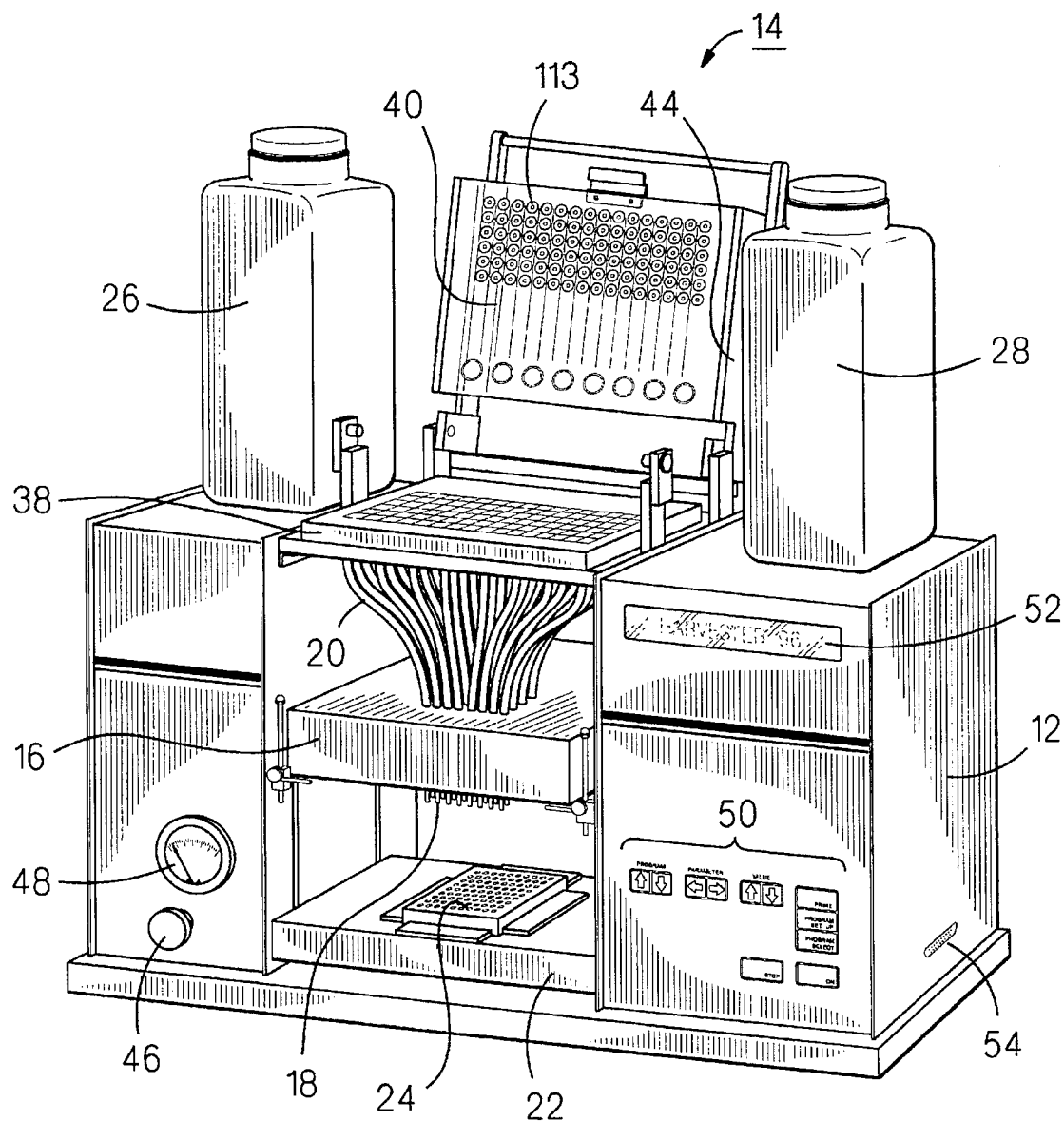
FIG. 1 is an enlarged perspective view of an embodiment of a cell harvester system according to the present invention.

Referring now to the Drawing, FIG. 1 is a perspective view of the cell harvester system of the present invention, generally indicated by the reference numeral 10. System 10 includes a housing 12 on which housing is fixedly mounted an upper assembly (shown in open position), generally indicated by the reference numeral 14, and on which is adjustably mounted a lower assembly 16 from the lower surface of which downwardly protrude aspirator tubes, as at 18. Upper and lower assemblies 14 and 16 are operatively connected by flexible tubes, as at 20. An elevatable platform 22 on which a multiwell laboratory tray 24 may be positioned is movable to raise the laboratory tray from a low position (shown on FIG. 1) to a high position (shown in fragmentary cross-section on FIG. 2). Provided on housing 12 are wash solution reservoirs 26 and 28. Other wash solution reservoirs (not shown) may also be part of system 10.

Upper assembly 14 includes a filter plate 38 fixed to an upper surface of housing 12 and a screen plate 40 and a cover plate 42 attached to hinged frame 44, the latter two plates being rotatable to close and clamp shut the upper assembly.

Mounted in housing 12 are control knob 46 for adjusting the pressure of air to wash solution reservoirs 26 and 28 and a gauge 48 for indicating the pressure thereof. A microprocessor/controller (not shown) is mounted internally of housing 12 and is operator-programmed by means of input keys 50 and provides visual information on display 52. Communication port 54 is provided to connect the microprocessor/controller to other control and/or data processing equipment (not shown).

Figure 2:
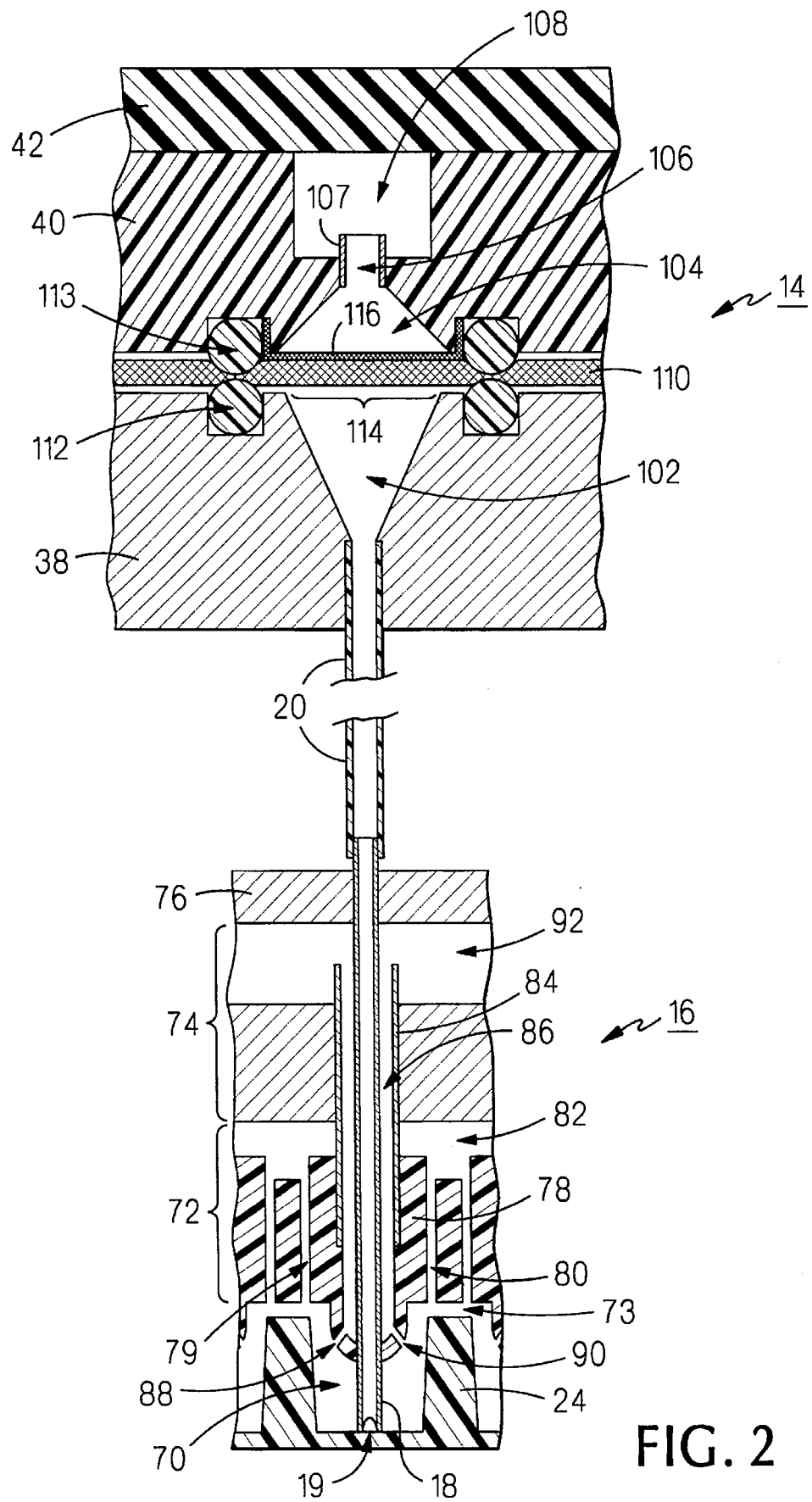
FIG. 2 is an enlarged cross-sectional view of the major flow path elements in the cell harvester system.

Referring now to FIG. 2, in which upper assembly 14 is shown in closed position, laboratory tray 24 has been raised so that aspirator tube 18 extends to the bottom of a well 70 of the laboratory tray. Aspirator tube 18 has a notch 19 defined in the lower end thereof for communication between the inside of the tube and well 70. Lower assembly 16 includes an overflow manifold plate 72 adjacent the upper surface of which is a wash manifold plate 74 and adjacent the upper surface of the latter is a cover plate 76.

Aspirator tube 18 is partially embedded in a molded tip 78 in which are defined slots 79 and 80 extending between the upper perimeter of well 70 and an overflow manifold 82 defined in overflow manifold plate 72. An annular space or "ring" 73 is defined between tray 24 and overflow manifold plate 72, which preferably has a height on the order of 0.040–0.060 inch. Also embedded in molded tip 78 is a wash solution tube 84 in which aspirator tube 18 is concentrically disposed such that an annular passageway 86 is defined between the wash solution tube and the aspirator tube for communication between wash solution orifices 88 and 90 defined in the lower end of molded tip 78 and a wash solution manifold 92 defined in wash manifold plate 74.

Figure 3:
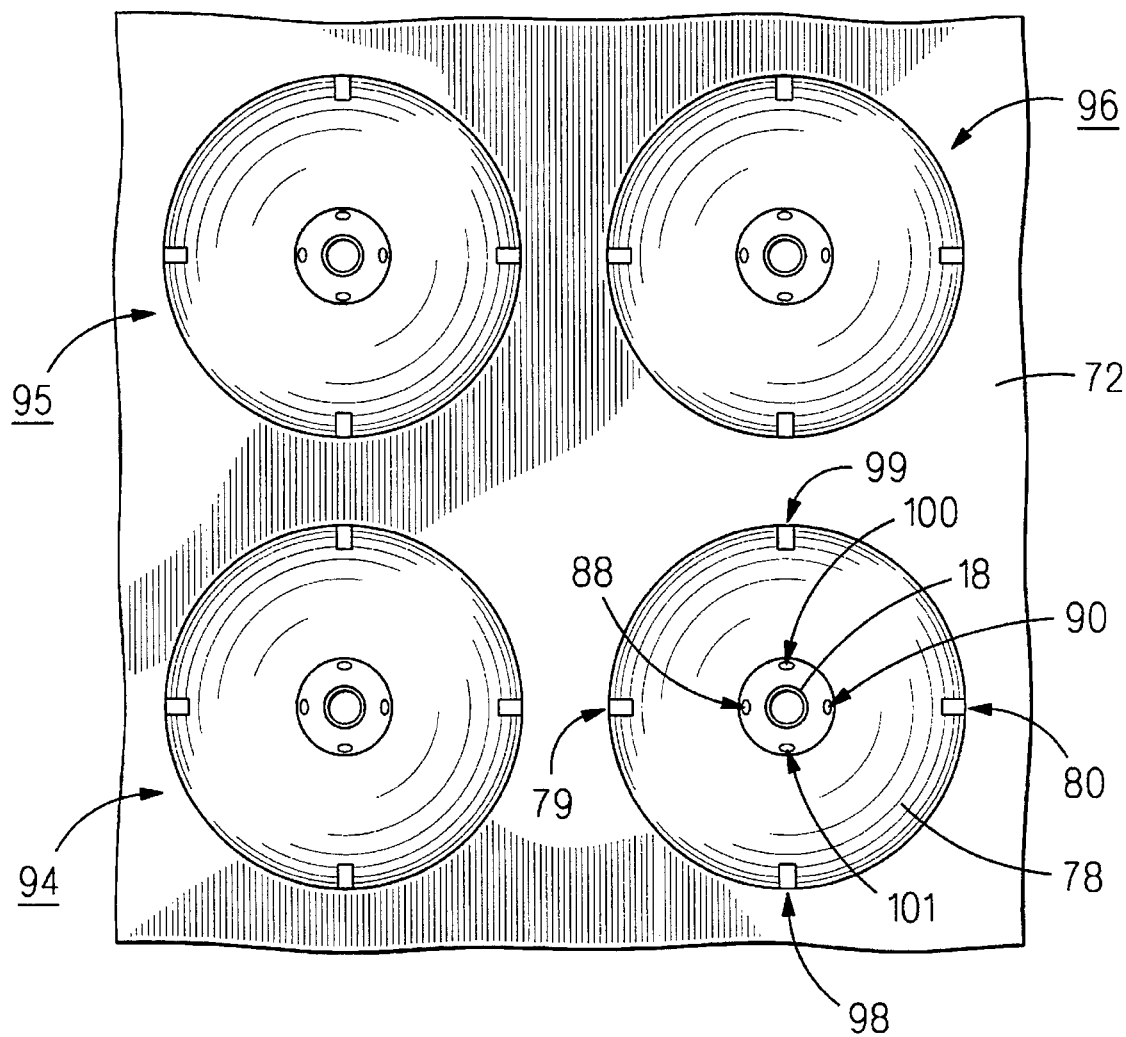
FIG. 3 is an enlarged bottom plan view looking up of the ends of aspirator assemblies mounted in an overflow manifold plate of the cell harvester system.

Reference to FIG. 3 will further show how aspirator tube 18 and molded tip 78 are held within overflow manifold plate 72, where they are but one set of a plurality of sets of aspirator tubes and molded tips, the others shown on FIG. 3 being generally indicated by the reference numerals 94-96. It can be seen on FIG. 3 that there are two additional slots 98 and 99 defined in the outer periphery of molded tip 78, so that there are four equally spaced slots defined in the periphery thereof for communication between ring 73 and overflow manifold 82 (FIG. 2). Likewise, there are two additional wash solution orifices 100 and 101 defined in the outer periphery of the lower end of molded tip 78, so that there are four equally spaced orifices defined in the periphery thereof.

Referring again to FIG. 2, the upper end of aspirator tube 18 extends through cover plate 76 for attachment thereto of the lower end of flexible tube 20, the upper end of which flexible tube extends into filter plate 38 of upper assembly 14 to a chamber 102 defined in the upper portion of the filter plate. Another chamber 104 is defined in the lower portion of screen plate 40 opposite chamber 102. A passageway 106 defined in screen plate 40 permits communication between chamber 104 and an aspirate manifold 108 defined in the screen plate. A tube 107 is disposed in passageway 106 and extends above the bottom of aspirate manifold 108 to prevent liquid within the aspirate manifold from flowing into chamber 104. Disposed between filter plate 38 and screen plate 40 is a filter mat 110. Circling chambers 102 and 104, respectively, and compressing filter 110 outside the outer peripheries of the chambers are oppositely disposed O-rings 112 and 113. A plurality of O-rings in screen plate 40, such as O-ring 114 may be seen on FIG. 1. O-rings 112 and 113 create a center filter area 114 separated from the rest of filter 110 by the clamping pressure of the O-rings. A cup-shaped backup screen 116 is disposed against the upper surface of filter mat 110.

Figure 4:
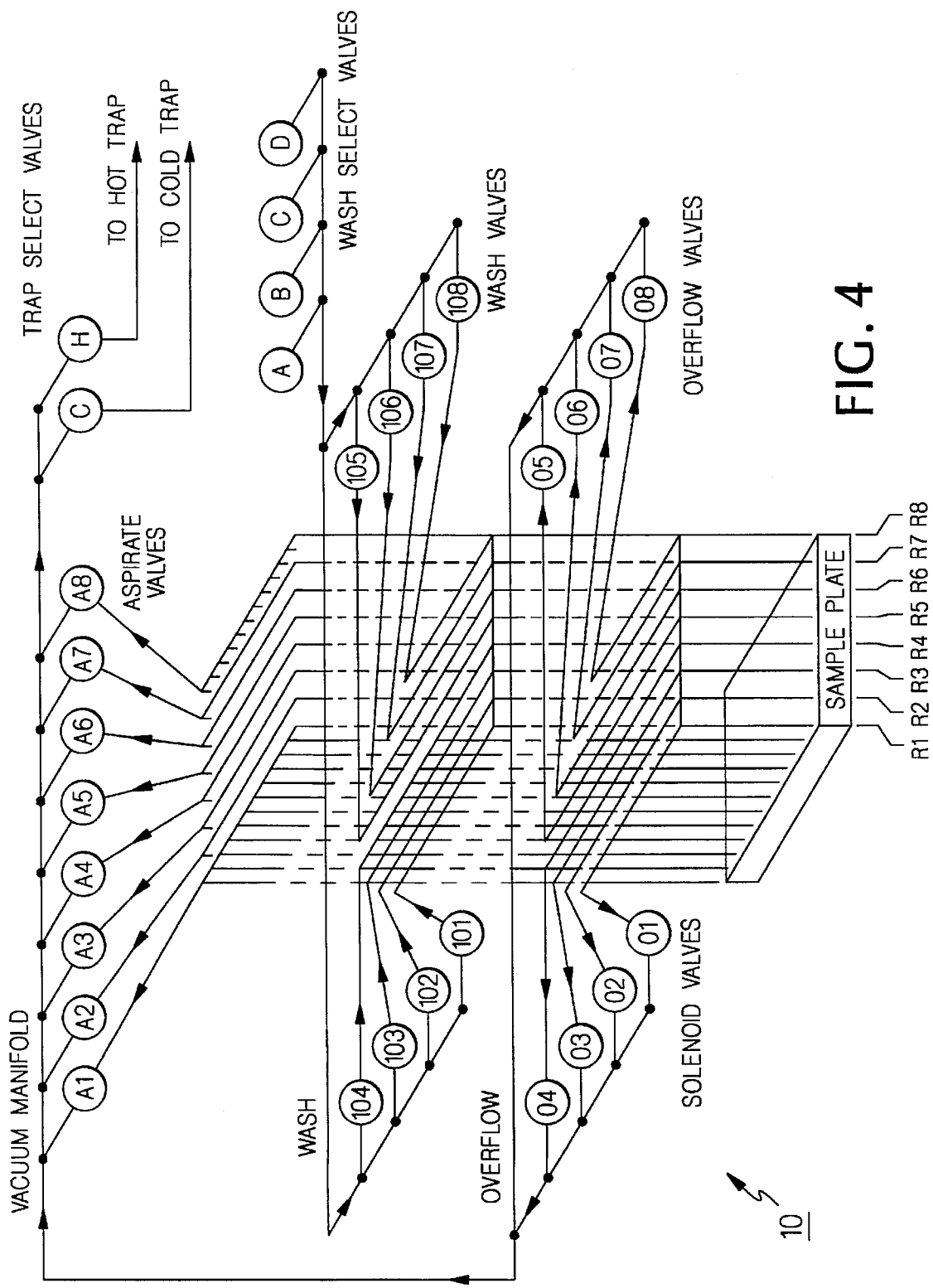
FIG. 4 is a perspective schematic flow diagram of the liquid flow paths in the cell harvester system.

FIG. 4 illustrates schematically on a perspective flow diagram how system 10 is connected to provide wash, overflow, and aspirate functions to a sample plate, here a 96-well sample plate having eight rows of wells, R1–R8, with twelve wells in each row. Inspection of FIG. 4 will show that the separate functions are manifolded so that each row of wells may be serviced individually independently of the other rows of wells. For example, overflow valves 01–08 determine which of rows R1–R8 will have overflow removal at any given time. Likewise, which row or rows are being washed is determined by wash valves W1–W8 and which wells are being aspirated is determined by aspirate valves A1–A8. It will be understood that, for example, the appropriate valves may be set so that rows R1, R4, R5, and R8 are being simultaneously washed and aspirated, while rows R2, R3, and R6 are being washed with overflow recovery, while there is no activity with row R7.

With further reference to FIG. 4, it is seen that one of a plurality of wash solutions may be chosen through wash select valves A–D. It will be understood that it is also within the contemplation of the present invention, with obvious changes to the flow diagram, to provide a system in which separate wash solutions may be chosen for each row of wells as well as to provide other groupings of wells in sets. Aspirate and overflow are removed from system 10 through the vacuum manifold through either of trap select valves C or H to a "hot" trap or a "cold" trap. The hot trap would be selected for radioactive materials and the cold trap would be selected for nonradioactive materials. The latter arrangement minimizes the quantity of waste radioactive material.

Figure 7:
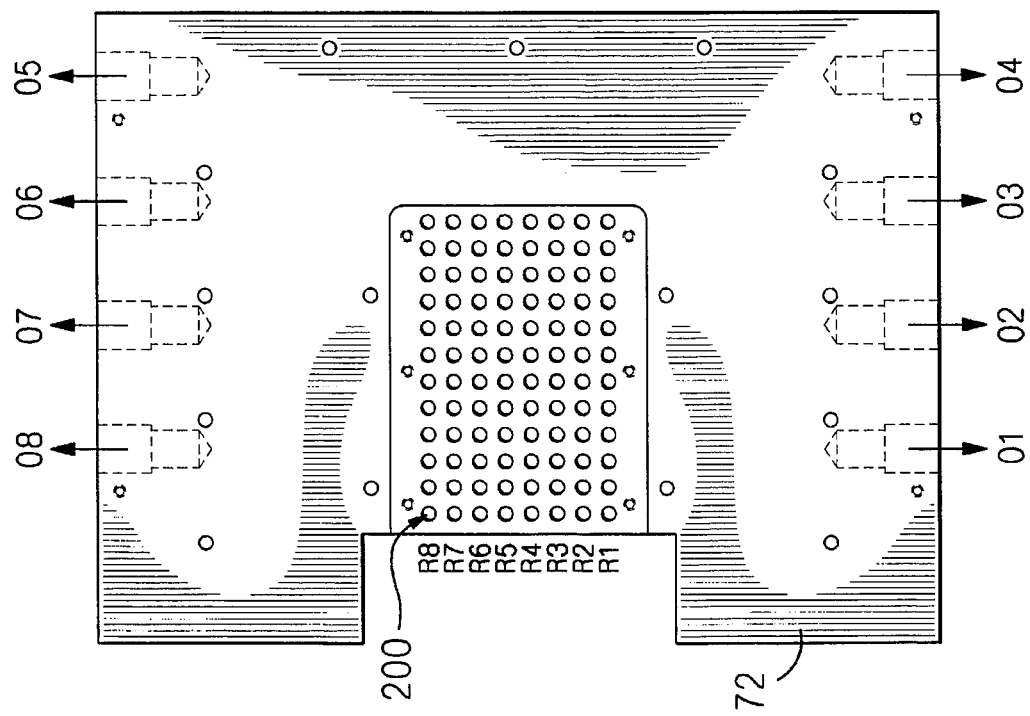
FIGS. 5, 6, and 7 are top plan, end elevation, and bottom plan views, respectively, of the overflow manifold plate of the cell harvester system.
Figure 6:
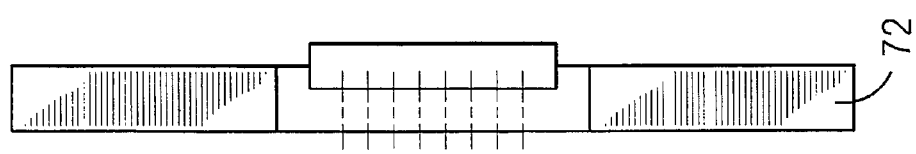
Figure 5:
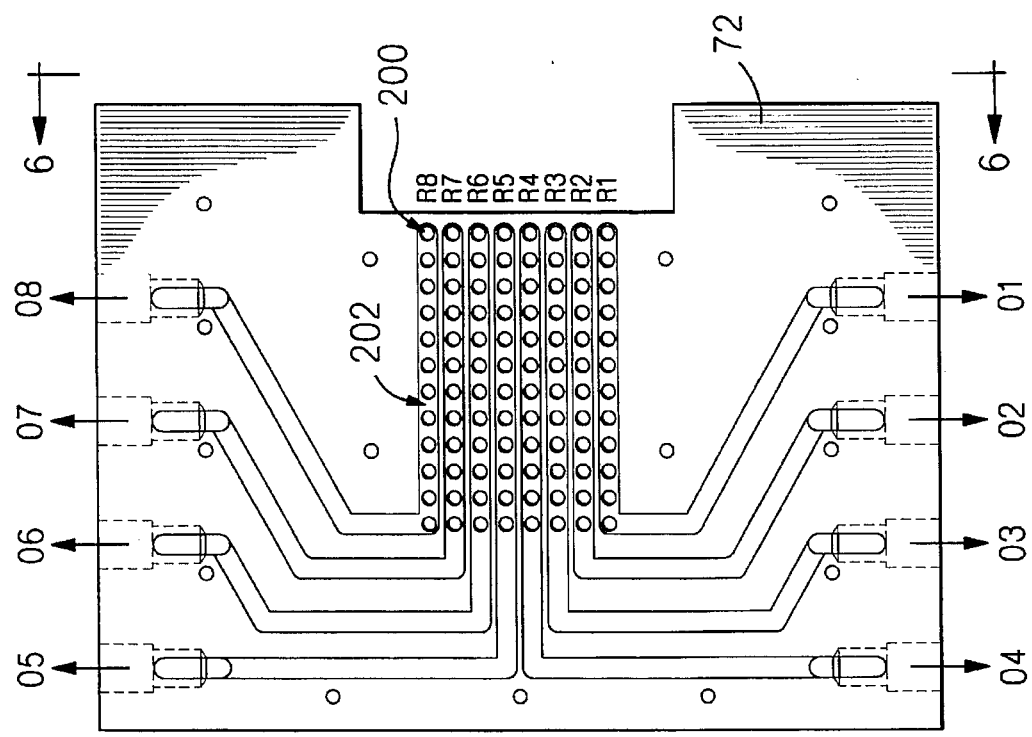

FIG. 5 is a top plan view, FIG. 6 is a cross-sectional view, and FIG. 7 is a bottom plan view looking up of overflow manifold plate 72 as configured for harvesting a 8×12 sample tray as indicated on FIG. 4. The nomenclature for valves and rows is the same as used on FIG. 4. Defined in plate 72 are a plurality of holes, such as hole 200 disposed in row R8, into which hole a molded tip carrying an aspirate tube (neither shown) would be fitted. Each of the holes in row R8 is disposed along a manifold 202 which leads to overflow valve 08. The balance of the 96 holes in plate 72 are disposed in their respective manifolds which lead to their respective overflow valves.

Figure 8:
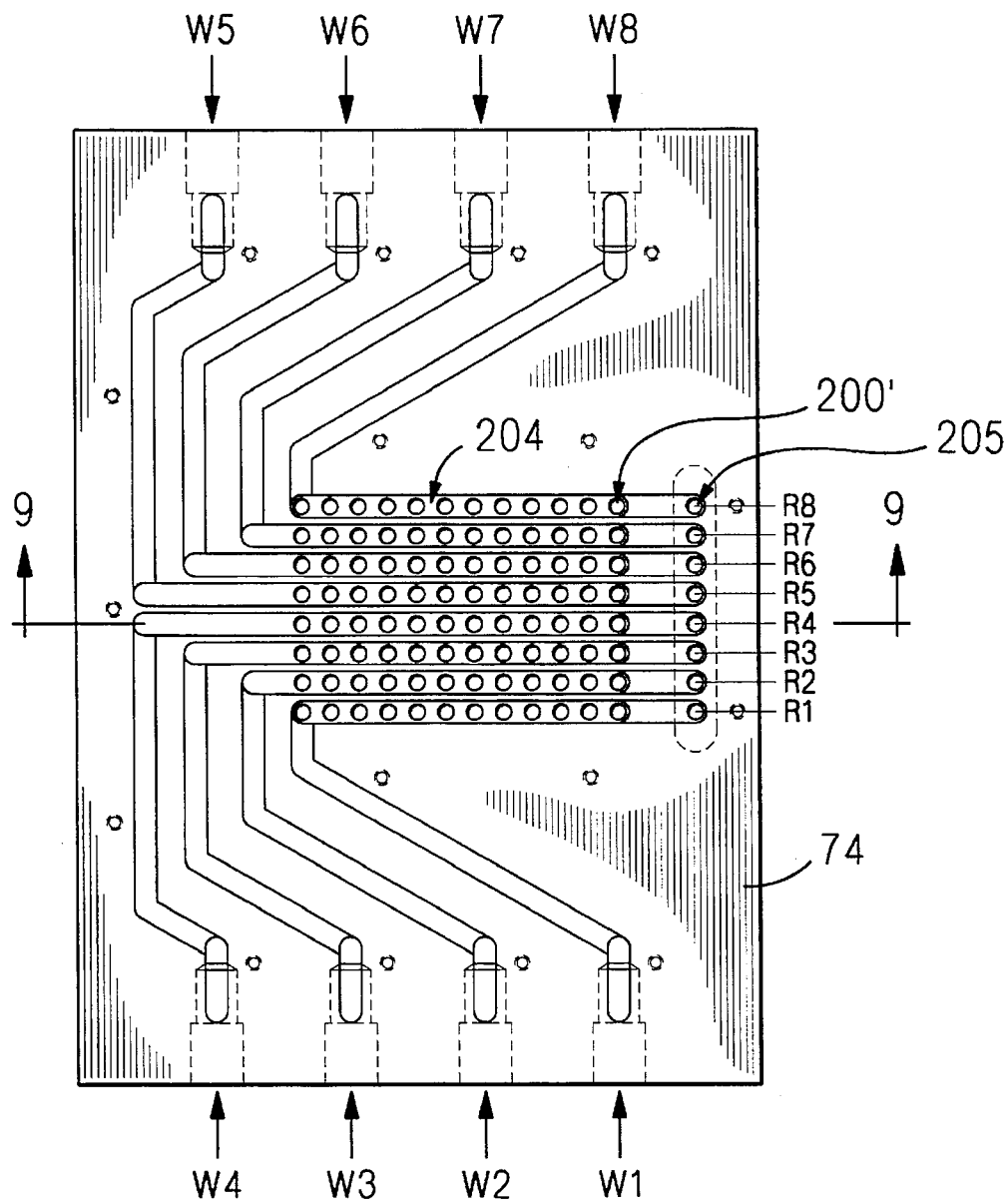
FIGS. 8 and 9 are top plan and cross-sectional views, respectively, of the wash manifold plate of the cell harvester system.
Figure 9:
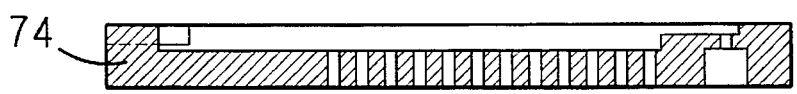

FIG. 8 is a top plan view of wash manifold plate 74, and FIG. 9 is a cross-sectional view thereof, which plate has a layout similar to that of overflow manifold plate 72. Here, a hole 200' would concentrically mate with hole 200 of FIG. 5 to form a continuous passageway. Hole 200' lies in wash manifold 204 which leads from wash valve W8. Defined in wash manifold plate 74 is a line of eight holes, such as hole 205 in the end of manifold 204, which are for venting the manifolds so that wash solution may enter the manifolds.

Overflow manifold plate 72, wash manifold plate 74, and cover plate 76 are sealed together by means of an adhesive, the type of which may be any conventional adhesive known in the art which is compatible with the liquids being handled.

Figure 10:
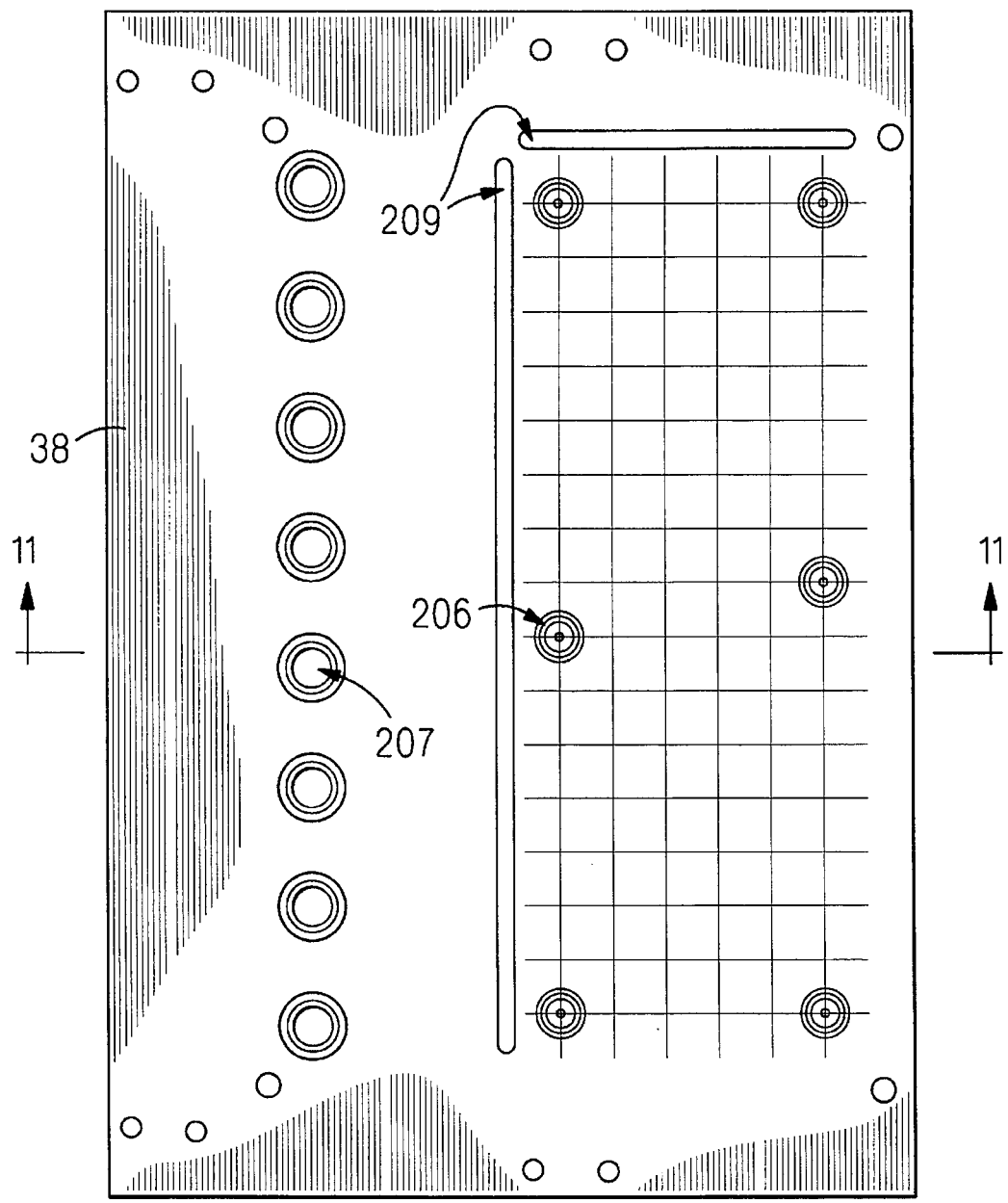
FIGS. 10 and 11 are top plan and cross-sectional views, respectively, of the filter plate of the cell harvester system.
Figure 11:
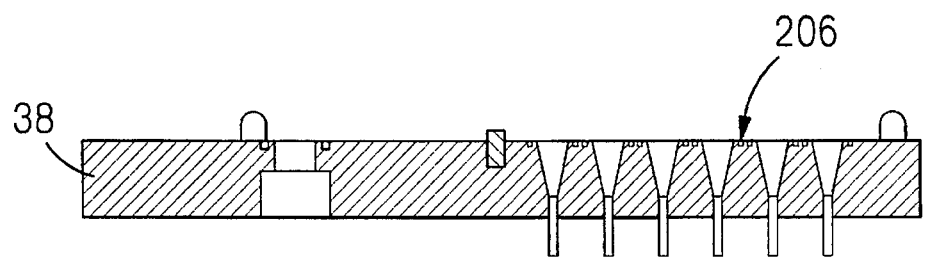

FIG. 10 is a top plan view of filter plate 38, and FIG. 11 is a cross-sectional view thereof. It can be seen that the 8×12 arrangement of the overflow manifold plate 72 and wash manifold plate 74 has been reconfigured into a 6×16 arrangement. Plate 38 has defined therein a plurality of grooves, as at 206, to accept O-rings therein (not shown). (A row of eight holes, such as hole 207, are continuations of holes from screen plate 40 on FIGS. 12–14.) Grooves 209 defined in filter plate 38 assist in the locating of the filter mat (not shown).

Figure 12:
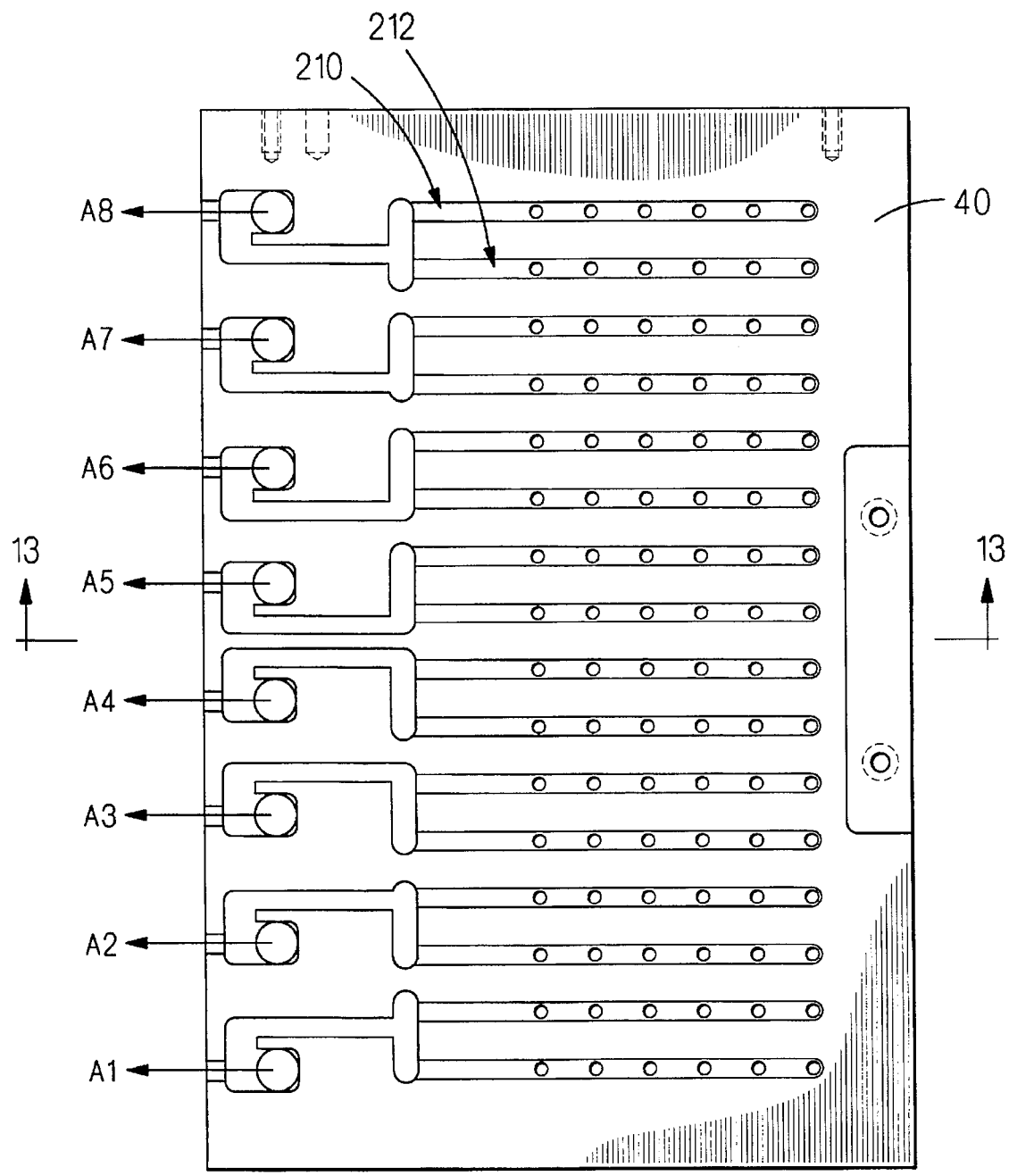
FIGS. 12, 13, and 14 are top plan, cross-sectional, and bottom plan views, respectively, of the screen plate of the cell harvester system.
Figure 13:
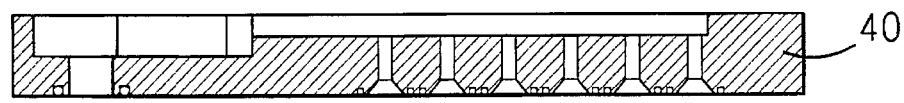
Figure 14:
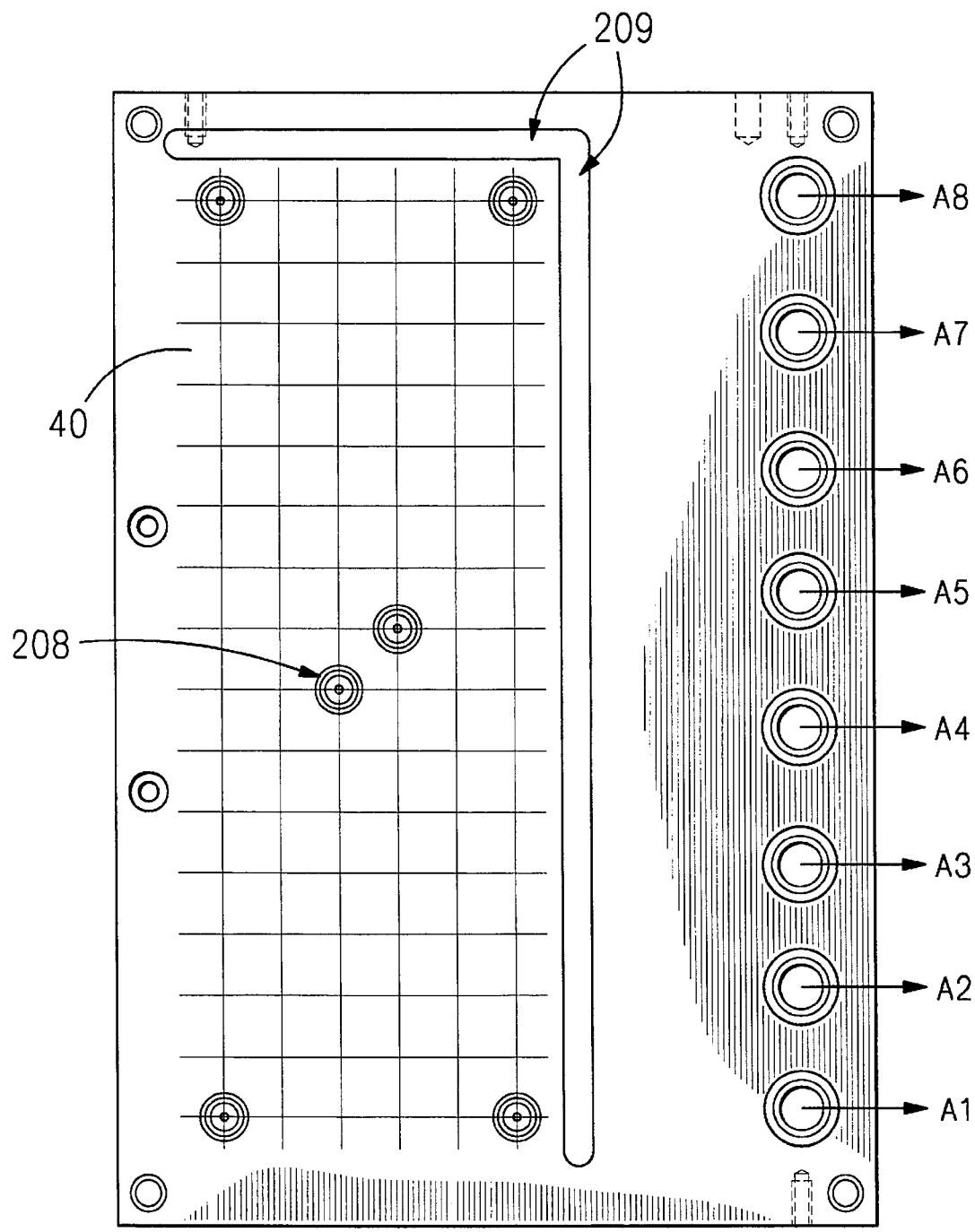

FIG. 12 is a top plan view, FIG. 13 is a cross-sectional view, and FIG. 14 is a bottom plan view looking up of screen plate 40, the latter showing a plurality of grooves, as at 208, to accept O-rings therein (not shown). Reference to FIG. 12 will show how the aspirate manifolds of the 6×16 configuration are arranged in pairs so that each aspirate valve serves 12 wells. For example, aspirate manifolds 210 and 212 are connected to lead to aspirate valve A8, so that all wells in row R8 (FIGS. 4, 5, and 8) are aspirated together.

Referring again to FIG. 2, it will be understood that, if the configuration of the wells in upper assembly 14 is the same as the configuration of wells in lower assembly 16, e.g., both 8×12, then aspirator tube 18 could extend straight into chamber 102 without the need for flexible tube 20.

It can be seen that overflow ring 73 allows any overflow to be aspirated away from the rim of well 70, thus preventing flow into adjacent wells. This is advantageous over conventional methods of overflow aspiration which rely on a single tube. Air to provide the aspiration comes from around laboratory tray 24.

Figure 17:
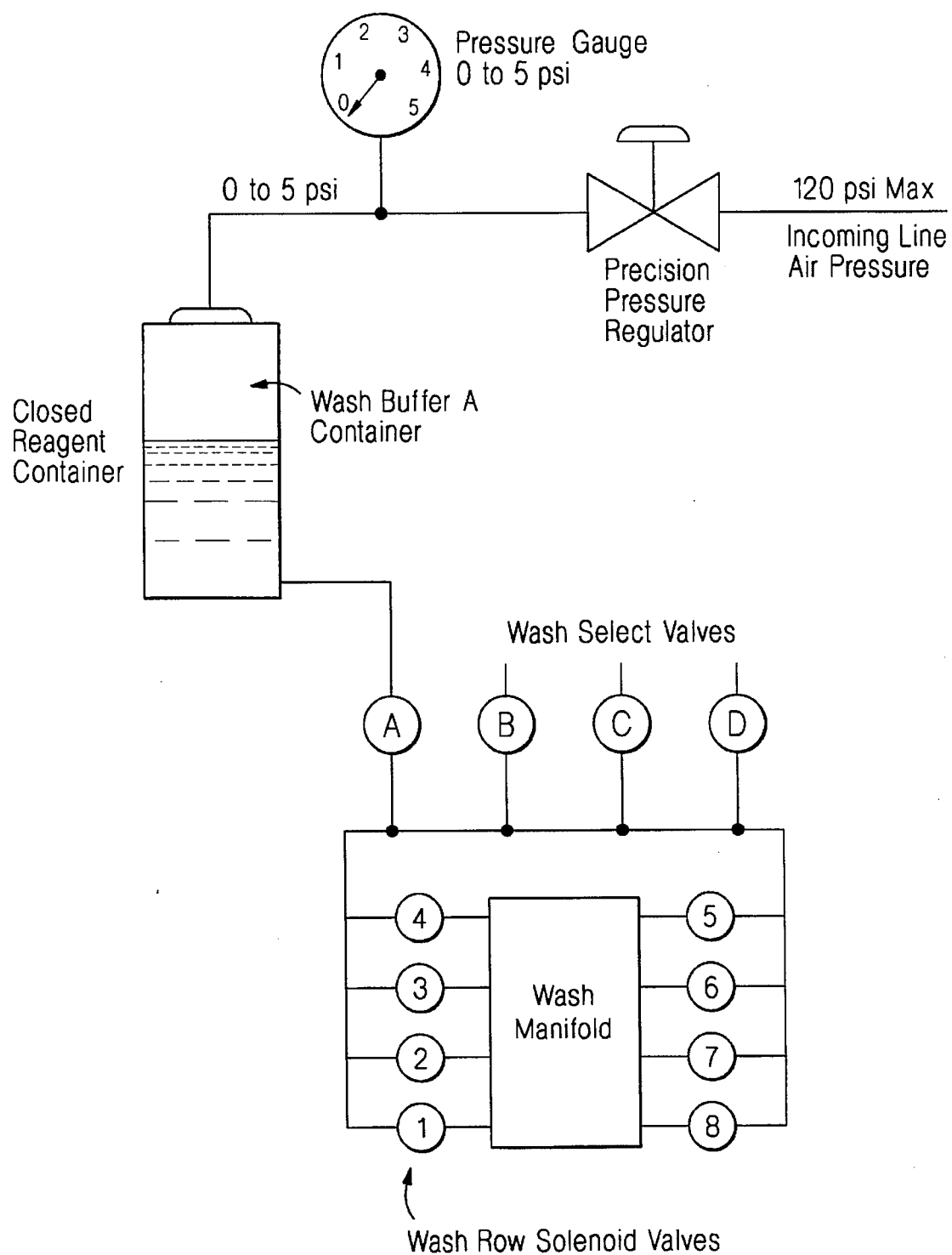
FIG. 17 is a schmematic flow diagram showing the pressurized wash solution system of the present invention.

Providing positive pressure on wash solution reservoirs 26 and 28 assures a good supply pressure of the wash solutions without use of conventional pumping methods or reliance solely on gravity. (See FIG. 17.) This also permits better control of the flow rates of the wash solutions.

O-rings 112 and 113 may be of any suitable material compatible with the materials handled and may be Buna-N rubber of about 70 Durometer hardness. With typical filter mat materials such as fiber glass or cellulose, it has been found that, with sufficient clamping pressure, O-rings 112 and 113 pinch filter mat 110 from both surfaces, thus defining a specific area of the filter mat and isolating that area from adjacent areas.

In operation, filter mat 110 is placed on filter plate 38 and screen plate 40 attached to cover plate 42 is clamped over it.

Figure 15:
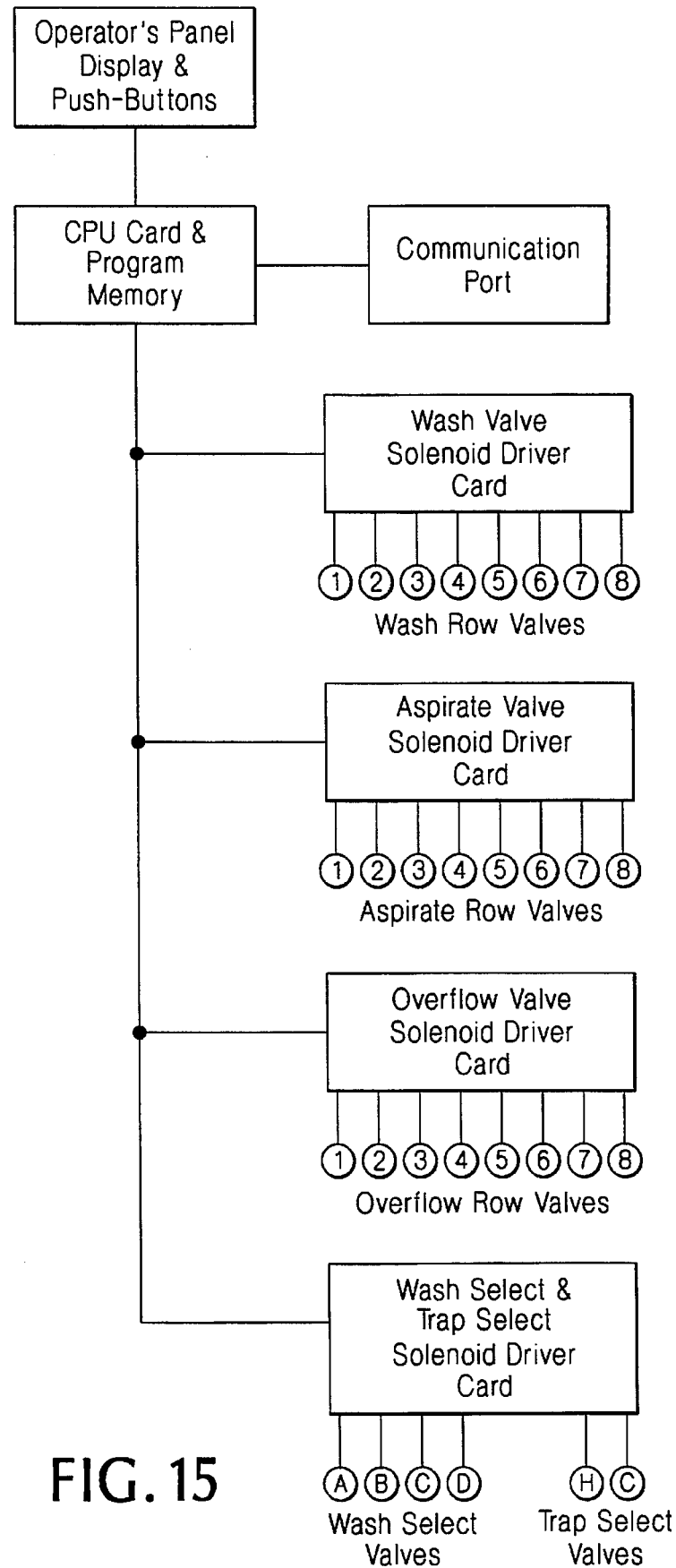
FIG. 15 is a block diagram of the control system of the cell harvester system.
Figure 16:
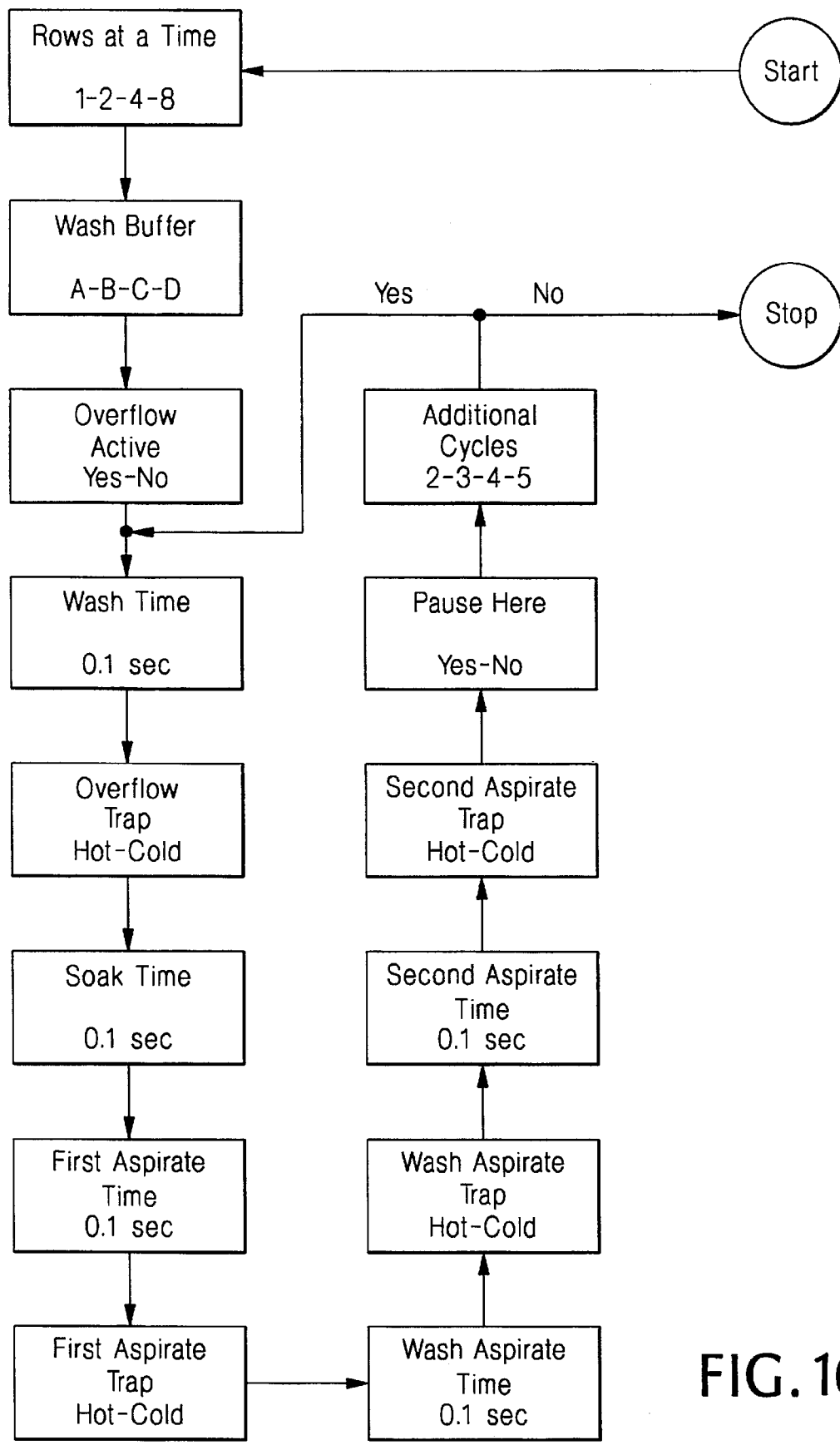
FIG. 16 is a block diagram showing the programming sequence of the controller of the cell harvester system.

Aspirator tips 18 are lowered into laboratory tray 24 and wash solution reservoirs 26 and/or 28 and/or other reservoirs are pressurized with air (0–5 psi). Prior to or following these steps, the microprocessor has been or will be programmed. A example of the operation of system 10 as shown on FIGS. 1–14 and described above is given below. Reference to FIGS. 15 and 16 should be made to assist in understanding the programming and operation of the system.

System 10 provides great flexibility in cell harvesting. All of the various parameters are individually controlled to enable the operator to set the optimum conditions for any protocol. System 10 as shown is designed to harvest from receptacles in the 8×12 array and 9 mm center-to-center distance of standard microplates. These may be individual microplates or microtubes arranged in the microplate format. When using microtubes other than standard microplates, it is necessary to extend the aspirate tubes 18 with adapter lengths of tubing (not shown).

As shown on FIG. 4, there are three sets of solenoid valves for each row of 12 wells. The program allows controlling these as individual sets or in groups.

The valves have the following functions:

Overflow Valve. Connects the overflow ring around each well to the vacuum source, to which the trap valves (hot or cold) are connected.

Wash Valve. Connects the wash orifices to the selected wash solution container.

Aspirate Valve. Connects the aspirator tube to the vacuum through the selected trap valve.

There are four wash selection solenoid valves, A, B, C, and D, which connect the desired wash container to the wash manifold. If valve A is selected, the wash container A is connected to the inlet of each of the 8 wash valves described above.

There are two trap selection solenoid valves. They determine which vacuum trap will collect the effluent on each sequence. This allows the operator to separate the waste stream into "hot" material, that must be disposed separately, and "cold" material, that can be disposed in a normal manner.

The microprocessor based control system allows 16 different programs to be created using combinations of these valves. These programs are individually set by the operator, and may be recalled for use at any time. Each time the program is selected, the operator may chose to run one or more of the sequences in that program.

To enter the programming mode, the PROGRAM push button is pressed. The PROGRAM SCROLL push button is pressed to scroll the display to the program number to be changed. Pressing the PARAMETER SCROLL push buttons provides the parameters, and pressing the VALUE SCROLL push button allows the operator to set the desired variables.

| PARAMETER DISPLAYED | VARIABLE TO BE SELECTED |
|---|---|
| Rows at a Time | 1, 2, 4, 8 |
| Overflow Active | Yes - No |

Example Sequence #1

| | Example Sequence #1 | |
|---|---|---|
| 1: | Wash Buffer | A - B - C - D |
| 1: | Wash Time | Time, 0.1 second intervals |
| 1: | Overflow Trap | Hot - Cold |
| 1: | Soak | Time, 1 second intervals |
| 1: | 1st Aspirate Time | Time, 0.1 second intervals |
| 1: | 1st Aspirate Trap | Hot - Cold |
| 1: | Wash/Aspirate Time | Time, 0.1 second intervals |
| 1: | Wash/Aspirate Trap | Hot - Cold |
| 1: | 2nd Aspirate Time | Time, 0.1 second intervals |
| 1: | 2nd Aspirate Trap | Hot - Cold |
| 1: | Pause Here | Yes - No |

Sequence #2, #3, #4 and #5

The same Parameters as outlined for Sequence #1 above may be set with their variable values.

The name of the program can be changed to any 12 letter name or mnemonic. This is accomplished as follows: After using the PROGRAM SCROLL push button to locate the desired program, the PARAMETER SCROLL button may scroll right or left. If scrolled right, the next parameter "Overflow Active" appears in the display. However, if it is scrolled left, then the flashing cursor appears, and moves left to each character in the display. Stopping the cursor on a character allows that character to be changed by using the VALUE SCROLL push buttons.

DESCRIPTION OF PARAMETERS

Rows At A Time

Allows the operator to determine how many rows of 12 wells each are to be run at a time. The complete program is run for each of the selected rows, starting with Row A before going to the next. For example, if two rows at a time were selected, the entire program would be executed on rows A & B. Upon completing A & B, the program would automatically move to C & D, then E & F, and finally G & H. If all 8 rows are selected, then the complete program is executed on all 96 wells simultaneously.

Overflow Active

This opens the overflow valves during the wash period only. During the time the wash solution is flowing, vacuum is connected to the ring around the top of the well. Should the well overflow for any reason, the excess will be captured by the overflow ring, and carried directly to the trap selected.

The overflow valves may be opened only during the wash portion of the cycle. If selected, they stay on for one second following the wash to clear the overflow manifold. They are interlocked by the program so that they cannot open any time the aspirate function is on, i.e., Wash/Aspirate.

Wash Solution

Allows the selection of which wash solution container is going to be used for this sequence. If Wash A is selected for Sequence #1, and Wash B is selected for Sequence #2, the operator must be aware of the dead volume in the manifold system. This is a limitation on switching buffers within one program. However, this can be accomplished manually, using the pause function (see below).

Wash Time

Determines the length of time the wash valves are open and the wash flows. This adds wash to the wells of the microplate or microtubes. The operator must be careful not to over fill the wells. Trial and error will determine the correct setting for the desired application.

As mentioned above, the overflow function, if selected, is only active during this wash time period. The overflow is not active during any other part of the cycle.

If the wash function is not desired in a sequence, setting the wash time to zero will bypass it.

Overflow Trap

Allows the operator to choose the appropriate trap to receive overflow effluent.

Soak

This allows the wash liquid to remain in the wells for the soak time selected prior to being aspirated. Soak time is adjustable from 0 to 254 seconds in one second intervals. If set to "0", the Soak function is bypassed.

1st Aspirate Time

Opens only the Aspirate valve for the time period selected. If the 1st Aspirate function is not desired in a sequence, setting the time to zero bypasses it.

1st Aspirate Trap

Selects the "Hot" or "Cold" trap to be used to catch the effluent from this aspirate. There is a three-second delay following each trap selection change. This allows the aspirate manifold to reach full vacuum before the aspirate valves open.

Wash/Aspirate Time

Opens the wash and aspirate valves simultaneously. The wash will enter each well at the top from the orifices and it will wash down the well sidewalls to be simultaneously aspirated through the filter mat to the selected trap.

The operator must use care in setting the flow rates during the wash/aspirate. The rate of flow through the aspirate lines is determined by the available vacuum (which may decrease the longer it remains open) and the amount of restriction in the filter mat. If particulate matter is being aspirated, this flow rate may decrease.

The incoming flow rate of the wash buffer is determined by the pressure applied to the wash solution reservoirs. This flow rate must be less than the aspirate rate, or flooding will occur.

If the Wash/Aspirate function is not desired in this sequence, setting the time to zero bypasses it.

Wash/Aspirate Trap

Allows the selection of which trap is to be used to collect the effluent from this aspirate.

2nd Aspirate Time

Sets the time that only the aspirate valves are open. This is a final aspirate only, one which follows a Wash/Aspirate to dry the wells. Setting the time to zero bypasses this function.

2nd Aspirate Trap

Allows the selection of which trap is to be used to collect the effluent from this aspirate.

Pause Here

If selected, the cycle stops at this point. It waits until the operator presses RUN to continue on the rest of the program.

This function allows manual intervention into an otherwise automatic cycle. There are a number of uses for this function. For example, it may be desired to pre-wet the filter mat with a reagent prior to running the sample plate. A small tray of reagent may be placed on the stage and aspirated with one of the aspirate functions. A pause would allow the operator to remove the reagent tray and replace it with the sample tray.

Pressing "Run" would then execute the rest of the program.

Sequence #2, #3, #4, and #5

There are five sequences, or levels, in each program. Each sequence allows the setting of different values for each of the parameters listed above. If any parameter is not desired, it may be set to zero, effectively bypassing it.

When selecting a program to be run, the display will show a "1" in the right hand character. This determines how many sequences, or levels, in the selected program are to be run.

Using the VALUE SCROLL push buttons, the value of 1 may be changed to 2, 3, 4, or 5. Thus, program #4 could be used, with sequences 1 through 3 for one application, and sequences 1 through 5 for another.

SAMPLE PROGRAM

Assume the following sequence of events is desired in a protocol that "Betty" uses for her work.

The filter mat is first pre-wet with alcohol. The sample is to be aspirated to the filter mat, and then washed with buffer.

The first part of the aspirate will contain a higher level of radioactivity and cannot go down the sink drain. On subsequent washes the radioactivity will be low and may drain into the sink.

Since this program will have one primary user, we will change the display from the default setting of "Program #3" to show the user's name (in this example "Betty"). We will set the following variables for the parameters. The wash buffer to be used will be in container A.

| Rows At A Time | 8 |
|---|---|
| Overflow Active | Yes |

Sequence #1

| 1: | Wash Buffer | A |
|---|---|---|
| 1: | Wash Time | 0.0 |
| 1: | Overflow Trap | Cold |
| 1: | Soak | 0 |
| 1: | 1st Aspirate | 1.0 |
| 1: | 1st Aspirate Trap | Cold |
| 1: | Wash Aspirate | 0.0 |
| 1: | Wash Aspirate Trap | Cold (Don't Care) |
| 1: | 2nd Aspirate Time | 0.0 |
| 1: | 2nd Aspirate Trap | Cold (Don't care) |
| 1: | Pause Here | Yes |

This portion of the cycle gives us one aspirate going to the cold trap, and then the cycle will stop. Thus, the operator can place a small tray of alcohol on the stage and have it aspirated through the filter mat for one second, with the effluent going to the cold trap. When the cycle stops, the alcohol tray is removed and replaced with the sample plate. Pressing RUN will let the "Betty" program continue on as follows:

Sequence #2

| 2: | Wash Buffer | A |
|---|---|---|
| 2: | Wash Time | 0.0 |
| 2: | Overflow Trap | Hot |
| 2: | Soak | 0 |
| 2: | 1st Aspirate | 0.3 |
| 2: | 1st Aspirate Trap | Hot |
| 2: | Wash/Aspirate | 0.3 |
| 2: | Wash/Aspirate Trap | Hot |
| 2: | 2nd Aspirate | 0.5 |
| 2: | 2nd Aspirate Trap | Hot |
| 2: | Pause | No |

This portion of the program will aspirate the sample to the filter mat, then wash the wells with a small amount of buffer, followed with a second aspirate to dry the wells. All effluent will go to the "Hot" trap. There is no pause, so the cycle continues to Sequence #3 as follows.

Sequence #3

| 3: | Wash Buffer | A |
|---|---|---|
| 3: | Wash Time | 0.0 |
| 3: | Overflow Trap | Cold |
| 3: | Soak | 0.0 |
| 3: | 1st Aspirate | 0 |
| 3: | 1st Aspirate Trap | Cold |
| 3: | Wash Aspirate | 2.0 |
| 3: | Wash Aspirate Trap | Cold |
| 3: | 2nd Aspirate | 1.0 |
| 3: | 2nd Aspirate Trap | Cold |
| 3: | Pause Here | No |

This portion of the program will wash and aspirate buffer through the well for two seconds, followed with a one-second drying. All effluent goes to the cold trap. Since this completes the example protocol, Sequence #4 and #5 will not be used. When selecting the "Betty" program the operator would select 3 sequences.

Materials of construction for system 10 may be any suitable for the liquids contacted. For example, overflow manifold plate 72 may be constructed from hard anodized aluminum. Wash manifold plate 74, cover plate 76, and filter plate 38 may be constructed from aluminum. Screen plate 40 and cover plate 42 may be constructed from acrylic polymer plate. Molded tips 78 may be constructed from polycarbonate. The solenoid valves may be constructed from stainless steel with a nickel plating. Tubing 20 may be inert polyethylene, with stainless steel tubes at the ends.

It will thus be seen that the objects set forth above, among those made apparent from the preceding description, are efficiently attained and, since certain changes may be made in the above construction without departing from the scope of the invention, it is intended that all matter contained in the above description or shown on the accompanying drawing is illustrative only e interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. In a cell harvester system of the type including means for harvesting samples from a plurality of generally vertical cells on a laboratory tray, each of said plurality of cells having a wall and an upper perimeter, an improvement, comprising:

(a) an open space around the upper perimeter of each said cell above said wall of said cell;

(b) means to provide wash solution to each of said cells; and (c) means to aspirate said wash liquid from said open space if said wash liquid overflows said cell.

2. An apparatus for supporting a filter medium in a cell harvester of the type for harvesting samples from a plurality of cells on a laboratory tray, said filter medium having first and second parallel surfaces, comprising:

(a) first resilient means to be disposed against and pressed into said first surface of said filter medium, so as to define a selected area of said filter medium, the shape of said first resilient means providing the boundary of said selected area, said selected area operatively connected to receive a sample from a selected one of said plurality of cells;

(b) second resilient means to be disposed against and pressed into the said second surface of said filter medium, opposite to said first resilient means, said second resilient means having a shape congruent with the shape of said first resilient means; and (c) a support screen disposed against one of said first and second surfaces of said filter medium to support said selected area.

3. An apparatus for supporting a filter medium in a cell harvester, as defined in claim 2, wherein said first and second resilient means comprise O-rings held within annular grooves defined in flat plates.

4. An apparatus for supporting a filter medium in a cell harvester, as defined in claim 3, further comprising said support screen being held in place by the perimeter of said support screen being captured between one of said O-rings and a wall of said groove in which said one of said O-rings is disposed.

5. A method of harvesting samples from generally vertical cells in a laboratory tray, each of said cells having a wall and an upper perimeter at the distal end thereof, comprising:

(a) aspirating sample liquid from a plurality of said cells;

(b) providing an open space around said upper perimeter of each said cell above said distal end of said wall;

(c) then providing wash solution to each of said cells; and (d) aspirating said wash solution from said open space if said wash solution overflows said cell.

* * * * *